(12) United States Patent
Tong

(10) Patent No.: US 12,329,926 B2
(45) Date of Patent: Jun. 17, 2025

(54) ADJUSTABLE INSERTION DEVICE

(71) Applicant: MEDTRONIC MINIMED, INC., Northridge, CA (US)

(72) Inventor: Davy Tong, Thousand Oaks, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 1148 days.

(21) Appl. No.: 16/598,998

(22) Filed: Oct. 10, 2019

(65) Prior Publication Data

US 2021/0106751 A1   Apr. 15, 2021

(51) Int. Cl.
A61M 5/142 (2006.01)
A61B 5/00 (2006.01)
A61B 17/34 (2006.01)
A61M 39/02 (2006.01)
A61M 39/14 (2006.01)

(52) U.S. Cl.
CPC ....... *A61M 5/14244* (2013.01); *A61B 5/6846* (2013.01); *A61B 17/3421* (2013.01); *A61M 39/0247* (2013.01); *A61M 39/14* (2013.01)

(58) Field of Classification Search
CPC ...... A61M 2005/1585; A61M 39/0247; A61M 39/14; A61M 5/14244; A61M 5/46; A61B 17/3421; A61B 5/6846; A61B 2017/922; A61B 1/00147
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |

(Continued)

*Primary Examiner* — Nathan R Price
*Assistant Examiner* — Adam J. Cermak
(74) *Attorney, Agent, or Firm* — Fortem IP LLP

(57) ABSTRACT

Disclosed herein is an insertion device for installation of a medical device comprising a transcutaneous element. The insertion device includes a device holder for holding the medical device. The insertion device also includes an installation surface configured to contact the medical device so as to deploy the transcutaneous element of the medical device. The insertion device also includes an elastic installation element configured to apply a force to the installation surface so as to bring the installation surface into contact with the medical device. The insertion device also includes a tensioner configured to adjust the force applied by the elastic installation element to the installation surface.

16 Claims, 11 Drawing Sheets

(56) References Cited

U.S. PATENT DOCUMENTS

| | | |
|---|---|---|
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2004/0002682 A1* | 1/2004 | Kovelman ............ A61M 5/158 604/136 |
| 2005/0165403 A1* | 7/2005 | Miller ................ A61B 10/025 600/567 |
| 2007/0123819 A1 | 5/2007 | Mernoe et al. |
| 2010/0160861 A1 | 6/2010 | Causey, III et al. |
| 2011/0178461 A1* | 7/2011 | Chong ............. A61M 5/14248 604/151 |
| 2016/0206809 A1* | 7/2016 | Kamen ............ A61B 5/150022 |

* cited by examiner

ADJUSTABLE INSERTION DEVICE

TECHNICAL FIELD

Embodiments of the subject matter described herein relate generally to insertion devices for medical devices, for example insertion devices for sensors or infusion sets.

BACKGROUND

Individuals with type II diabetes have a resistance to insulin. As a result, the individual's muscle and fat cells take up less glucose than normal, and there is less insulin-mediated activities in the cells of that individual. The effects of type II diabetes can become medically serious if not correctly managed.

One way of managing this resistance to insulin is through the use of an insulin pump. Typically, insulin pumps are devices that allow for the delivery of insulin into the fatty tissue under the skin through the use of a cannula.

Insulin pumps typically include an insulin pump configured to meter the amount of insulin delivered from an insulin reservoir, an infusion set that allows for insulin to flow from the pump into the individual's tissue (usually subcutaneous fatty tissue) via a cannula, and tubing that connects the infusion set to the pump.

The correct installation of the infusion set onto an individual is important. An incorrectly installed cannula (such as a crimped cannula) may interrupt or block insulin delivery. In order to ensure the correct installation of the infusion set onto an individual, insertion devices are available. Known insertion devices are tools that assist with the installation of the infusion set onto the individual. Specific insertion devices are designed for specific infusion sets. Additionally, insertion devices may alternatively or additionally be used to install other types of medical device, for example analyte sensors, onto an individual. The correct installation of these other types of medical device, for example analyte sensors, is also important. In particular, an incorrectly installed analyte sensor, with an incorrectly installed sensor probe, may provide incorrect analyte measurements, such as incorrect sensor glucose measurements.

It is desirable to improve the ergonomics of existing insertion devices. It is also desirable to improve patient comfort when using an insertion device. Importantly, it is desirable to provide patients with the means to insert the cannula of an infusion set or the probe of an analyte sensor in a consistent manner for a wide range of patient body types.

Furthermore, other desirable features and characteristics will become apparent from the subsequent detailed description and the appended claims, taken in conjunction with the accompanying drawings and the foregoing technical field and background.

BRIEF SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

According to a first exemplary embodiment, there is provided an insertion device for installation of a medical device. The insertion device includes a device holder for holding a medical device. The insertion device also includes an installation surface configured to contact the medical device so as to deploy a transcutaneous element of the medical device. The insertion device also includes an elastic installation element configured to apply a force to the installation surface so as to bring the installation surface into contact with the medical device. The insertion device also includes a tensioner configured to adjust the force applied by the elastic installation element to the installation surface.

According to a second exemplary embodiment, there is provided a method of using an insertion device to install a medical device. The method includes the step of inserting a medical device into a device holder of the insertion device. The method also includes the step of positioning the device holder against an installation site. The method also includes the step of pressing a button of the insertion device for a first time to install a transcutaneous element of the medical device held in the device holder of the insertion device. The method also includes the step of pressing the button of the insertion device for a second time to release the medical device from the insertion device.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

After a study of existing insertion devices, the present inventor recognized that the design of a specific insertion device for a specific medical device results in some disadvantages. In particular, and using the example of an infusion set as the particular medical device being installed, one disadvantage recognized by the inventor is that specific insertion devices are developed so as to as deploy the cannula of a specific infusion set with a specific, pre-determined amount of force and insertion speed. This amount of force and speed is pre-set when manufacturing the insertion device specific to a particular type of infusion set. It has been recognized by the inventor that the use of a pre-determined force to install the infusion device may not be sufficient for some users, or may be too painful for other users. More specifically, for users with thicker or tougher dermal layers and tissue, the pre-determined amount of force may not be sufficient to correctly install the cannula into the user. Conversely, the pre-determined amount of force may be excessive for other users. Similar problems arise with the use of specific insertion devices for installing transcutaneous elements of other medical devices, such as probes of analyte sensors.

In order to overcome this problem, exemplary embodiments provide an insertion device where the amount of force used to install a transcutaneous element of the medical device is variable.

Figure 1:
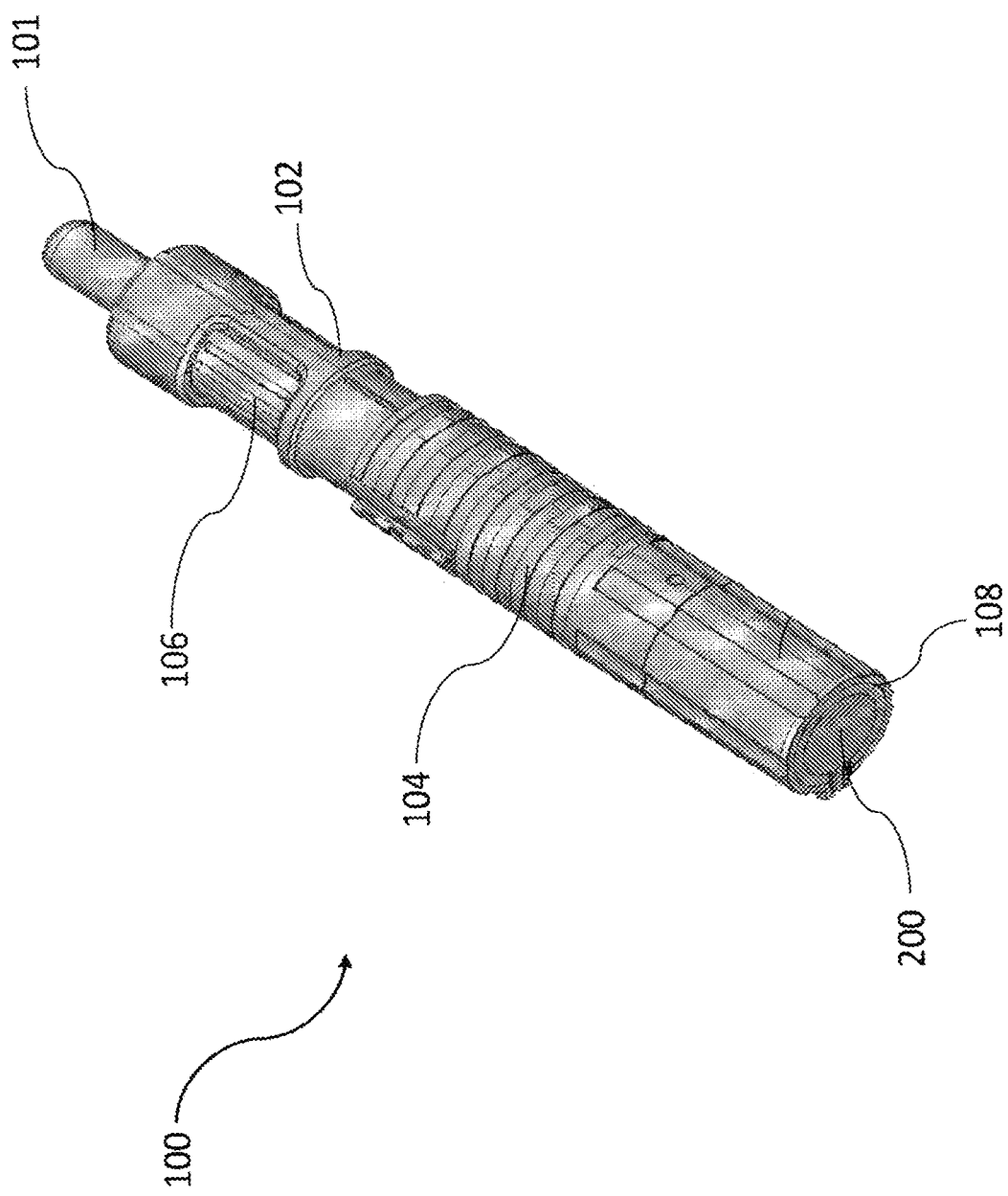
FIG. 1 is an isometric view of an insertion device according to exemplary embodiments.

An exemplary insertion device 100 is shown in FIG. 1. As can be seen in FIG. 1, the insertion device 100 includes a housing 102, an device holder 108 and a button 101 for deployment of an medical device 200, exemplified here as an infusion set, which is held in the device holder 108. Device holder housing 109 is disposed over the device holder 108. The insertion device 100 also includes a slide 104 which is movable longitudinally with respect to the housing 102 so as to "arm" the button 101 for deploying a transcutaneous element of the medical device, exemplified here as a cannula of the infusion set 200, as will be explained in more detail below. Although the below techniques will be described with reference to the installation of a cannula of an infusion set, it will be appreciated that the teaching may be applied equally to the installation of a transcutaneous element of other types of medical devices, such as a sensor probe of an analyte sensor, e.g., a sensor of a continuous glucose monitoring (CGM) device.

Figure 2:
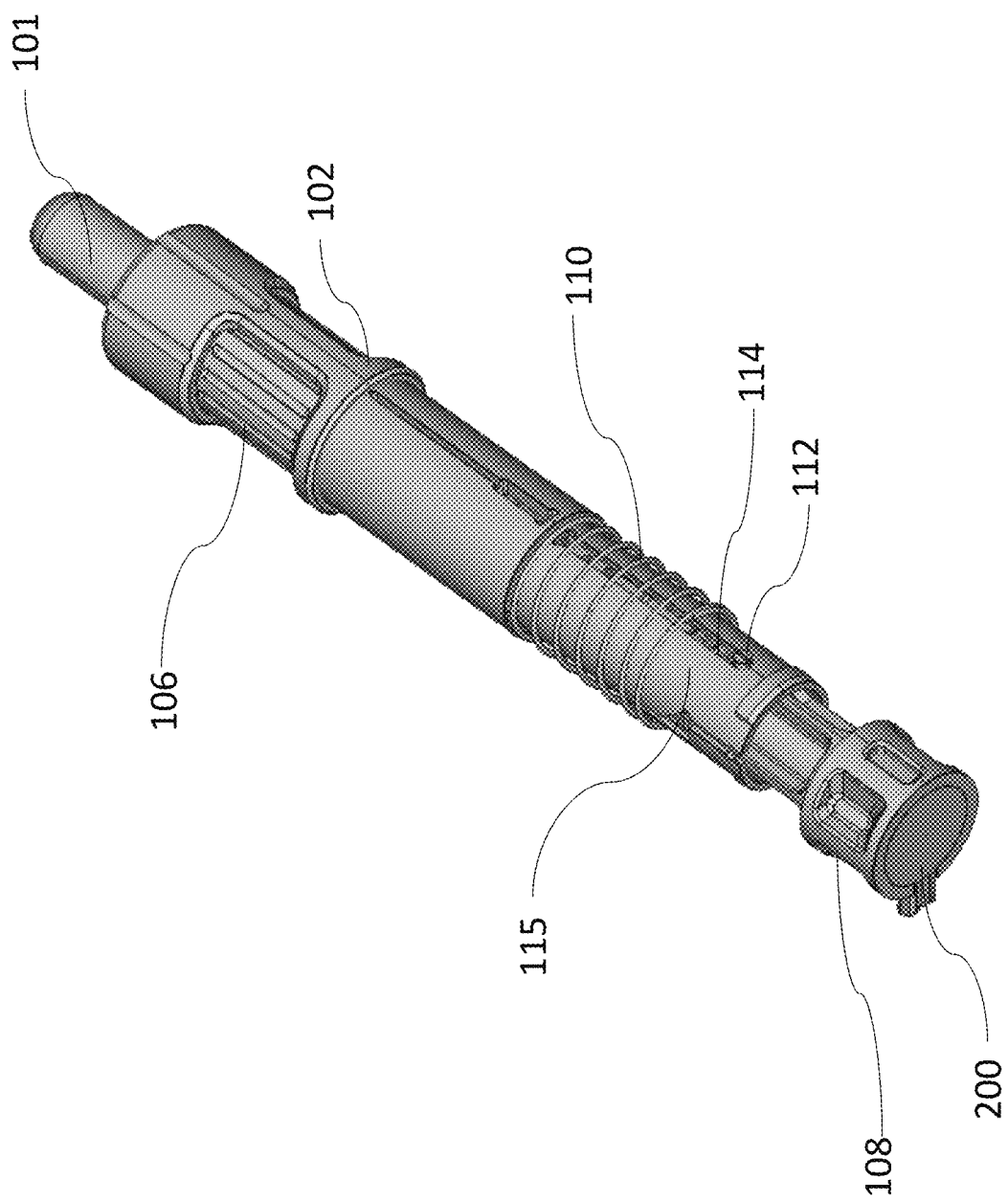
FIG. 2 is another isometric view of an insertion device according to exemplary embodiments.

FIG. 2 shows an isometric view of the insertion device 100 with the slide 104 and device holder housing 109 removed. As can be seen in FIG. 2, the medical device 200 to be installed, exemplified here as an infusion set is disposed in the device holder 108. As can also be seen in FIG. 2, the insertion device 100 includes an internal casing 115, which comprises a groove 114. A pin 112 is slidably disposed in the groove 114, which pin 112 is connected to an inner surface of the slide 104. As such, a longitudinal movement of the slide 104 along the insertion device 100 causes movement of the pin 112 in the groove 114.

The insertion device 100 further comprises a slide locating element 110, which is connected to an inner surface of the slide 104 and which is configured to bias the slide 104 toward a pre-determined position. The slide locating element 110 therefore causes the slide 104 to return to its initial position after a user effects a longitudinal movement of the slide 104. In exemplary embodiments, the slide locating element 110 comprises a spring.

Figure 3:
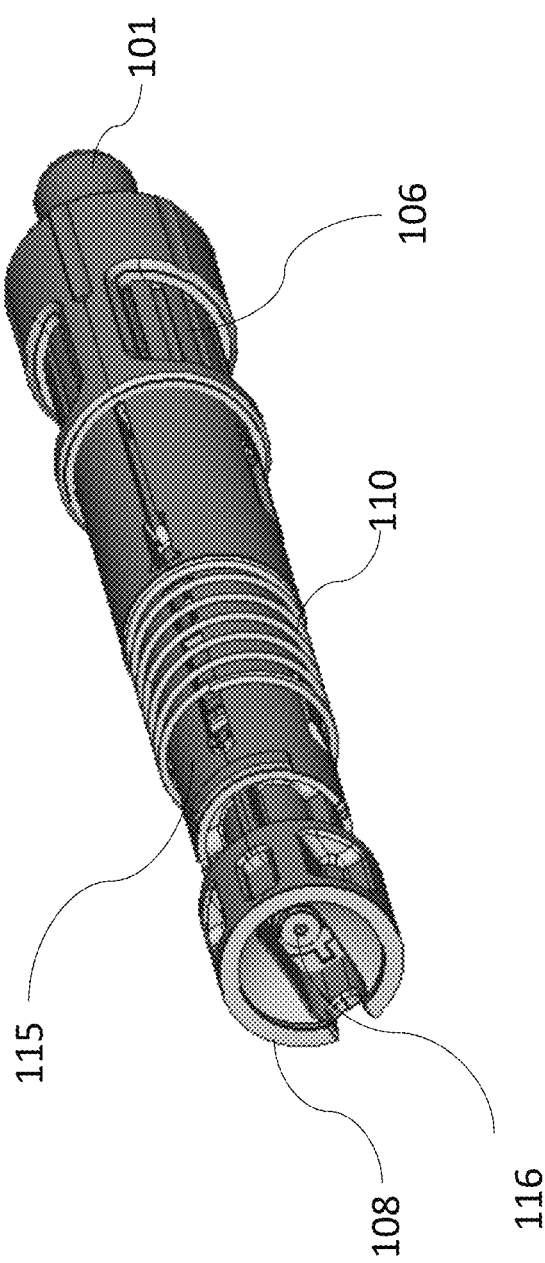
FIG. 3 is another isometric view of an insertion device according to exemplary embodiments.

Turning to FIG. 3, another isometric view of the insertion device 100 is shown. In this figure, no medical device 200 is held in the device holder 108. As can be seen in FIG. 3, an installation surface 116 is disposed proximate to the device holder 108. As will be described in more detail below, the installation surface 116 is configured to selectively apply force to a medical device 200, such as an infusion set, held in the device holder 108 so as to deploy a transcutaneous element of the medical device, such as the cannula of the infusion set or the probe of an analyte sensor. More specifically, the force applied by the installation surface 116 is configured to force the transcutaneous element of the medical device 200 through the user's skin and into subcutaneous tissue.

Figure 4:
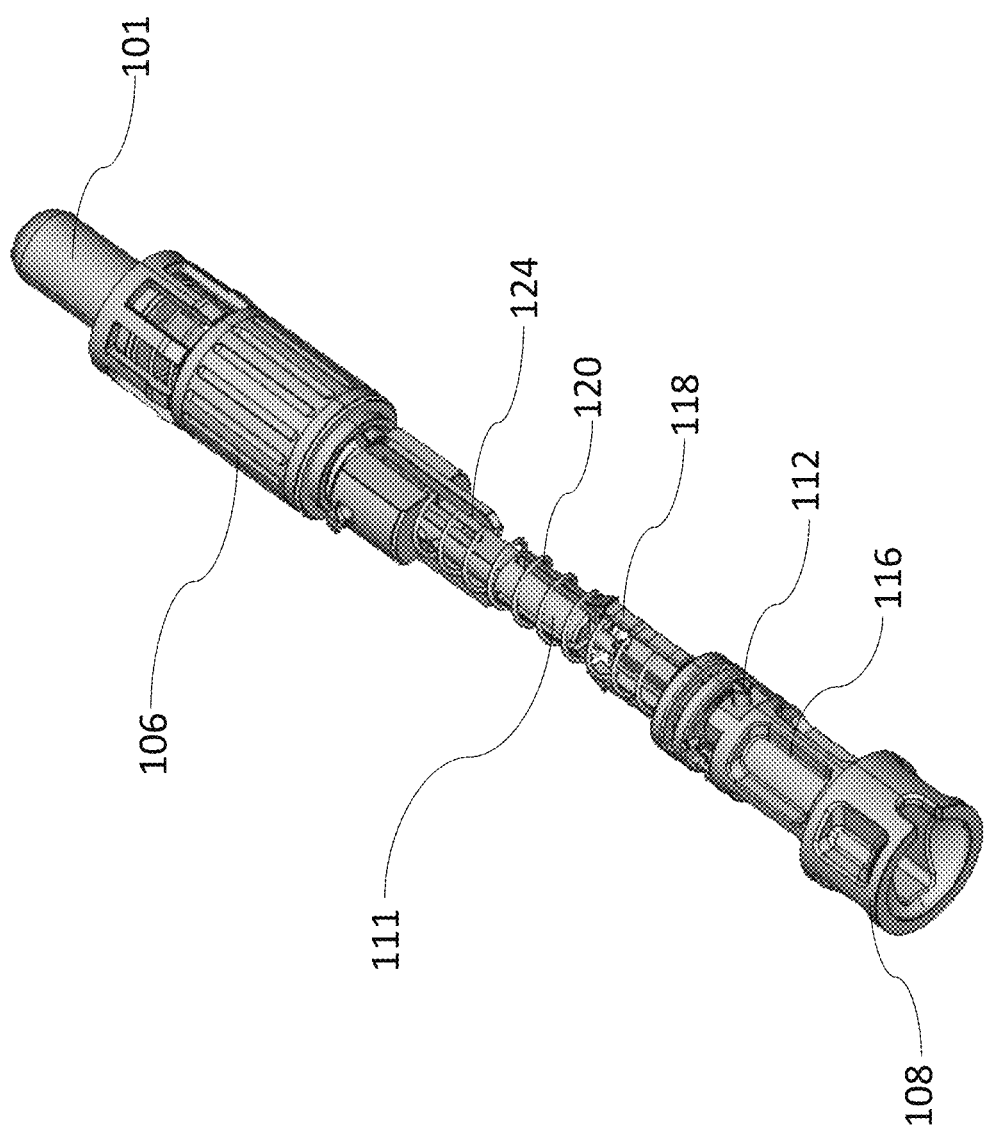
FIG. 4 is another isometric view of an insertion device according to exemplary embodiments.

FIG. 4 shows an isometric view of the insertion device 100 with the internal casing 115 removed. As can be seen in this figure, the installation surface 116 extends from a first end at a location proximate to the device holder 108 to a second end at a location distant from the device holder 108. The installation surface 116 is connected to the pin 112. As such, a longitudinal movement of the slide 104 away from the device holder housing 109 causes a movement of the pin 112 within the groove 114 away from the device holder 108, which causes a corresponding movement of the installation surface 116 away from the device holder 108.

The insertion device 100 also includes an elastic installation element 120 which is connected, at a first end thereof, to the installation surface 116. As can be seen in FIG. 4, as the installation surface 116 moves longitudinally away from the device holder 108, the elastic installation element is placed under tension/compression. In exemplary embodiments, the elastic installation element 120 is a spring, and is placed under compression by the installation surface 116 moving longitudinally away from the installation surface 116.

The insertion device 100 also includes one or more latches 118 connected to the installation surface 116. The one or more latches 118 are configured to mate with recesses provided on the inner surface of the internal casing 115 when the installation surface 116 has been moved a predetermined distance away from the device holder 108. In this manner, the elastic installation element 120 can be held under tension/compression by means of the mating of the one or more latches 118 to the recesses.

The insertion device 100 also includes one or more extension elements 124. As will be explained in more detail below, the one or more extension elements are operably connected to the button 101, such that depressing of the button 101 moves the one or more extension elements 124 longitudinally toward the device holder 108. The one or more extension elements 124 have an angular position such that each one of the one or more extension elements 124 can contact a respective one of the one or more latches 118 when the one or more extension elements 124 are moved toward the device holder 108 via depression of the button 101 and when the one or more latches 118 are in a mated configuration with the recesses of the internal casing 115.

When the one or more extension elements 124 are moved so as to contact the respective one or more latches 118 in this mated configuration, the one or more extension elements 124 bias the one or more latches 118 so as to move the latches 118 out of the mated configuration with the one or more recesses. When the latches 118 are moved out of this mated configuration, the installation surface 116 is no longer held in position by this mated configuration, and the energy stored in the compressed elastic installation element 120 is released, thereby moving the installation surface 116 rapidly toward the device holder 108.

When the installation surface 116 reaches the device holder 108, the installation surface is configured to contact an infusion set 200 held in the device holder 108 so as to install a transcutaneous element of the medical device, such as a cannula of an infusion set or a sensor probe of an analyte sensor.

As explained above, the present inventor recognized that the amount of force applied in the installation of the transcutaneous element, such as a cannula of an infusion set, may not be sufficient for some users (for example, those users with thicker skin and tissue), and may be too large for other users (for example, those who may consider this force to be too painful).

In order to adjust the force applied in the installation of the transcutaneous element, a user may rotate the rotating dial 106. By rotating the rotating dial 106, the amount of energy stored in the compressed state of the elastic installation element 120 is adjusted, as will be explained with reference to FIG. 5. By adjusting the amount of energy stored in the elastic installation element 120 in its compressed state, the amount of force applied in the installation of the transcutaneous element of the medical device can also be adjusted.

Figure 5:
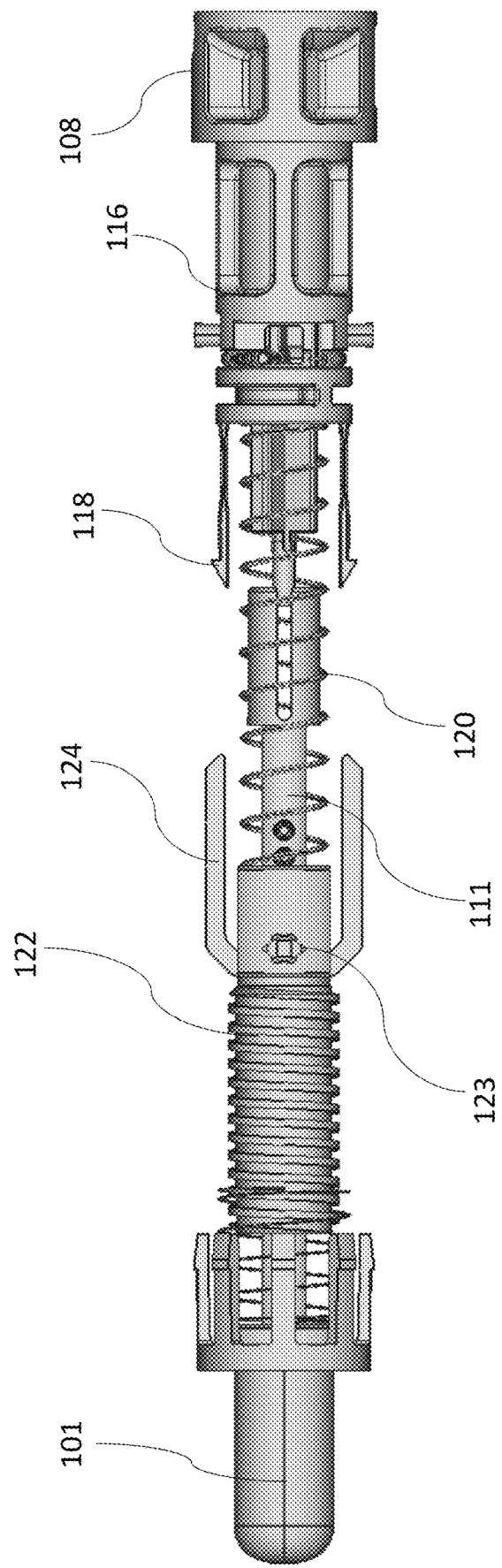
FIG. 5 is another isometric view of an insertion device according to exemplary embodiments.

FIG. 5 shows a view of the insertion device 100 which has the rotating dial 106 removed. As can be seen in FIG. 5, the rotating dial 106 is disposed over and connected to a tensioner 122. In exemplary embodiments, the tensioner 122 comprises an external screw thread that engages with a corresponding screw thread on the internal surface of the rotating dial 106. One end of the tensioner 122 is connected to an end of the elastic installation element 120. As a user rotates the rotating dial 106, the mating screw threads causes the tensioner 122 to move longitudinally toward or away from the device holder 108 along a central column 111. In exemplary embodiments, a clockwise rotation of the rotating dial 106 will cause the tensioner 122 to move longitudinally toward the device holder 108 along the central column 111, whilst an anti-clockwise rotation will cause the tensioner to move longitudinally away from the device holder 108 along the central column 111.

Movement of the tensioner 122 toward or away from the device holder 108 increases or decreases, respectively, the compression of the elastic installation element 120. In this manner, the amount of energy stored in the compressed state of the elastic installation element 120 can be adjusted by the user. By adjusting the amount of energy stored in the compressed state of the elastic installation element 120, the amount of force applied by the installation surface 116 during installation of the transcutaneous element of the medical device 200, such as the cannula of an infusion set, is also adjusted. The user is therefore able to select a force that effectively deploys the transcutaneous element of the medical device 200 with an acceptable amount of pain for that user.

Figure 6:
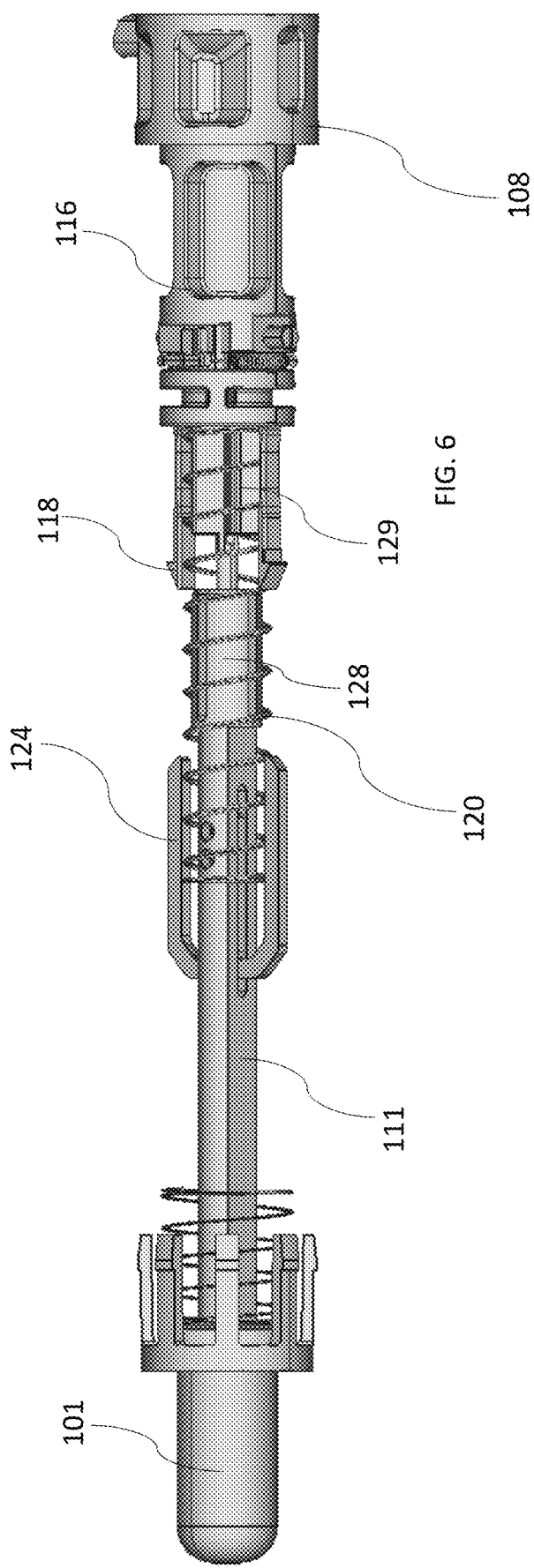
FIG. 6 is another isometric view of an insertion device according to exemplary embodiments.

Another view of the insertion device 100 is shown in FIG. 6, with the tensioner 122 removed. As can be seen in FIG. 6, the button 101 is connected to the extension elements 124 via a connection formed in the central column 111, such that the extension elements 124 are able to move independently from the tensioner 122.

As explained above, the present inventor also recognized the need for insertion devices to have a simple, ergonomic design. Many conventional insertion devices required multiple interactions with different parts of the device in order to complete installation of a medical device. In exemplary embodiments, the insertion device 100 allows for installation of a medical device and also release of the medical device from the insertion device 100 (thereby completing installation of the medical device) with consecutive button presses of a single button 101. In this manner, the installation of a medical device is made more user-friendly and ergonomic.

How the complete installation of the medical device 200 with a transcutaneous element in an ergonomic and simple manner is achieved through two presses of button 101 will now be explained. As explained above, after the user longitudinally moves the slide 104 away from the device holder 108 so as to compress the elastic installation element 120 and to mate the one or more latches 118 with corresponding recesses on the internal surface of the internal casing 115, the first press of button 101 causes the one or more extension elements 124 to release the one or more latches 118 from the recesses and to cause the elastic installation element 120 to apply force to the transcutaneous element of the medical device 200 via the installation surface 116. However, after the transcutaneous element of the medical device 200 is installed into the user, the medical device 200 itself remains held in the device holder 108.

Figure 7:
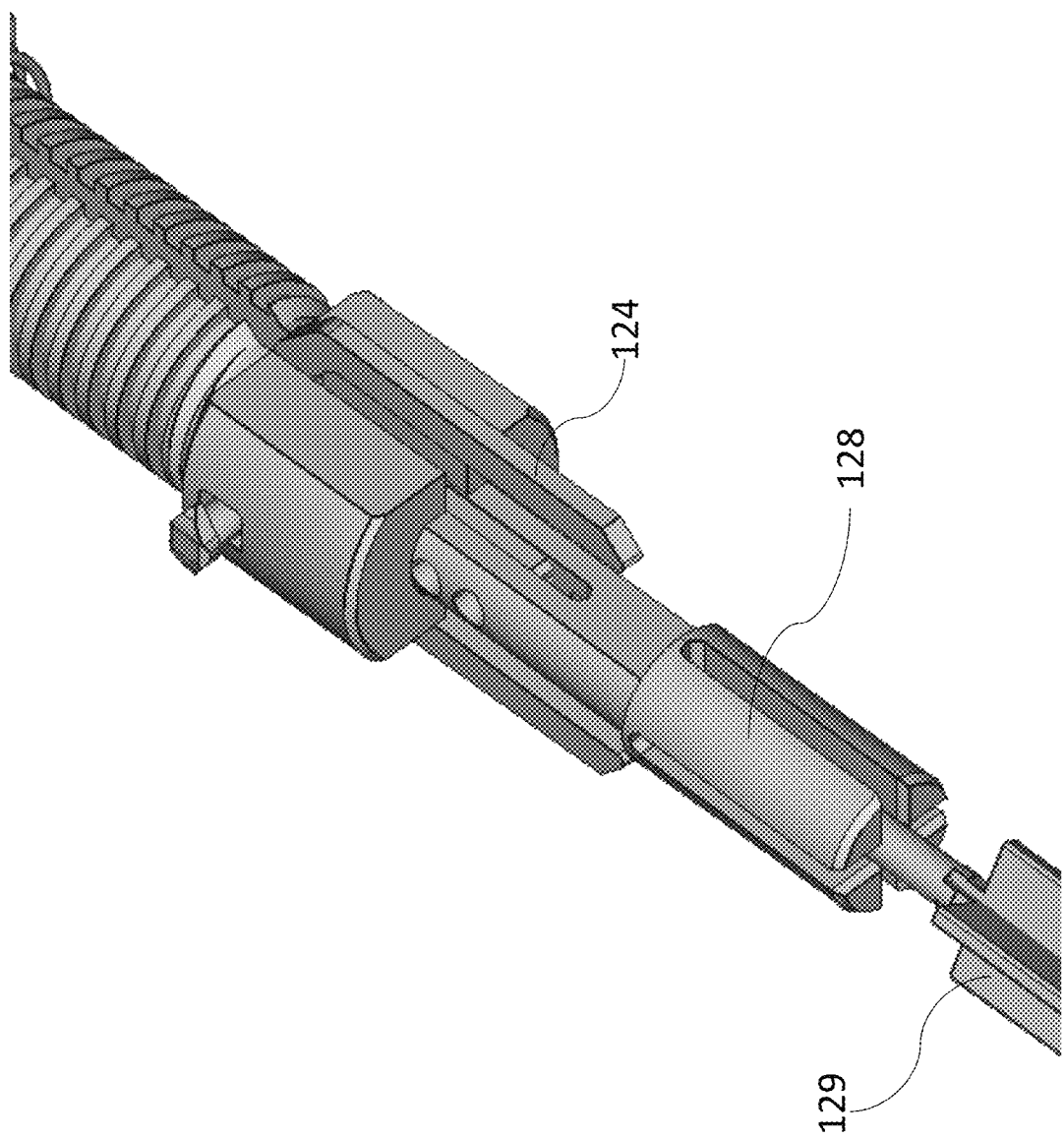
FIG. 7 is another isometric view of an insertion device according to exemplary embodiments.

In order to release the medical device 200 from the device holder 108, a second press of button 101 is required. The second press of button 101 causes engagement between a first rotation surface 128 and a second rotation surface 129. Additional views of the first rotation surface 128 and the second rotation surface 129 can be seen in FIGS. 7 and 8. The surfaces of the rotation surface 128 and the second rotation surface 129 are shaped such that, as the first rotation surface 128 moves longitudinally toward and engages with the second rotation surface 129, the second rotation surface is forced to rotate. As can be seen in FIG. 7, the second rotation surface 129 is connected to the device holder 108, which comprises one or more angled grooves 131. As the second rotation surface 129 rotates, the device holder 108 is also forced to rotate, and the one or more angled grooves 131 interact with the medical device 200 so as to force the medical device 200 away from the device holder 108, thereby releasing the medical device 200 from the device holder 108 and completing installation of the medical device 200.

Figure 8:
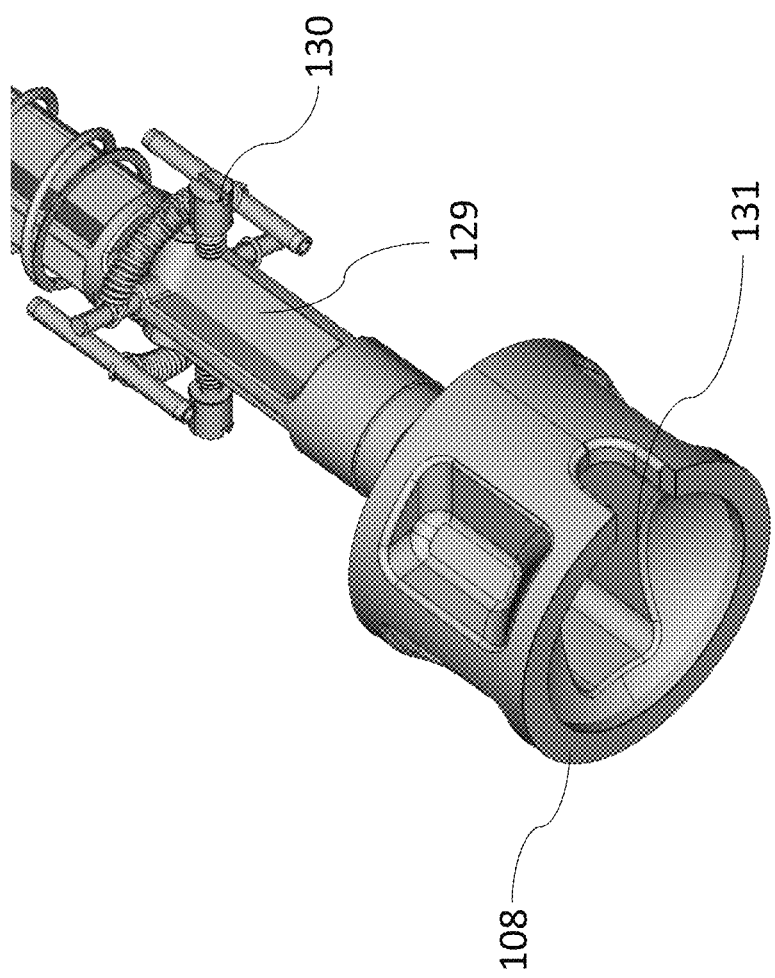
FIG. 8 is another isometric view of an insertion device according to exemplary embodiments.
Figure 9:
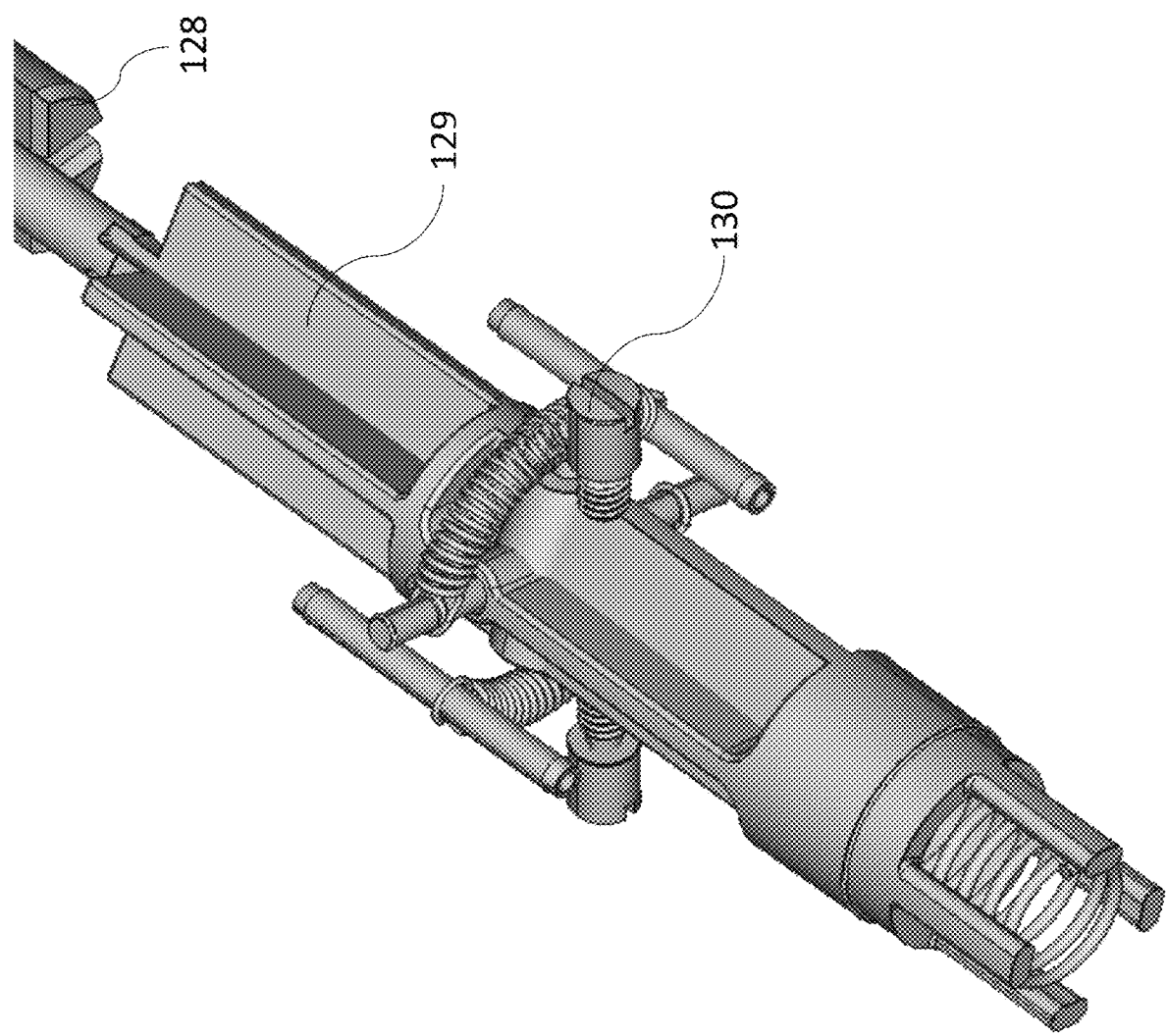
FIG. 9 is another isometric view of an insertion device according to exemplary embodiments.

As can also be seen in FIGS. 8 and 9, the insertion device 100 includes an elastic return element 130 configured to bias the second rotation surface 129 towards an un-rotated position. In use, as the user releases the second press of the button 101 and the first rotation surface 128 moves longitudinally away from and out of contact with the second rotation surface 129, the elastic return element 130 causes the second rotation surface 129 and consequently the device holder 108 to rotate back into an original rotational position. In an exemplary embodiment, the elastic return element 130 is formed from an arrangement of one or more springs. In an exemplary embodiment, an additional return element biases the first rotation surface 128 away from the second rotation surface 129 such that release of the button 101 causes separation of the first and second rotation surfaces.

In an alternative exemplary embodiment, rotation of the second rotation surface 129 does not rotate the device holder 108 but instead causes movement of another surface or component so as to force the medical device 200, for example an infusion set or sensor probe, out of the device holder 108.

Figure 10:
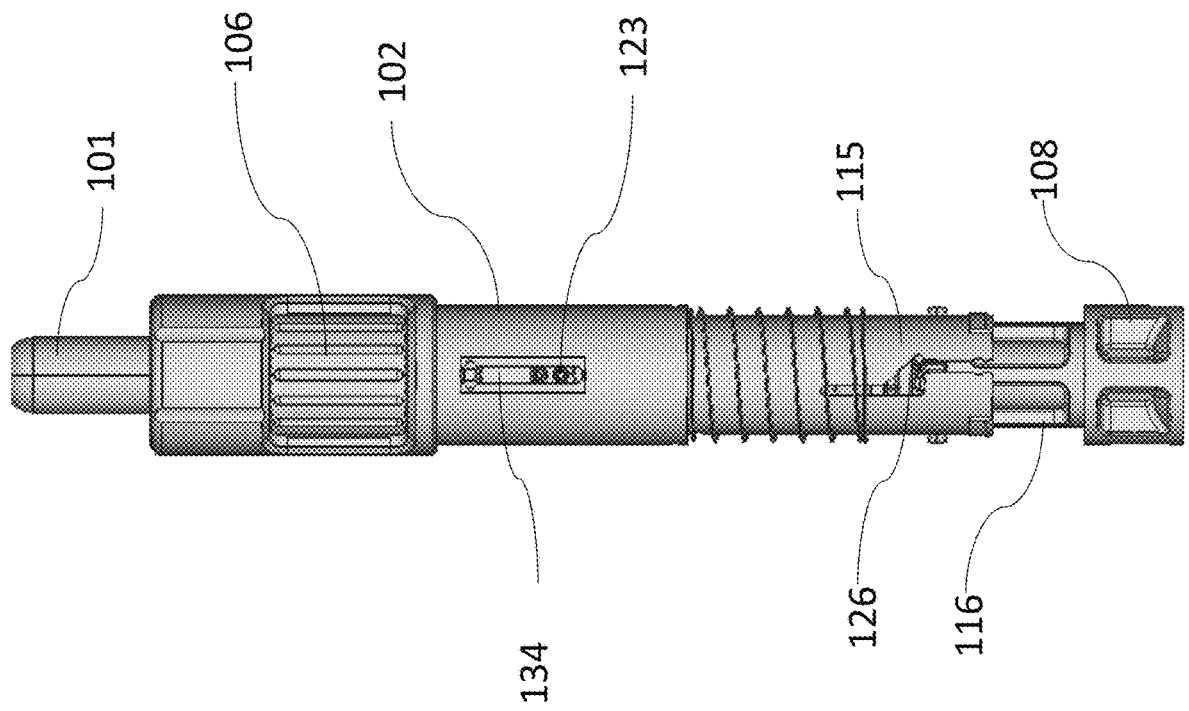
FIG. 10 is another isometric view of an insertion device according to exemplary embodiments.

Turning now to FIG. 10, a preferred embodiment of the insertion device 100 is shown. As can be seen in FIG. 9, the insertion device 100 preferably includes a tension indicator 123. The tension indicator 123 comprises a symbol or other identifier, for example a pin, that is disposed within a slot 134 in the housing 102. The tension indicator 123 is connected to the tensioner 122, as is shown in FIG. 5.

In this embodiment, movement of the tensioner 122 longitudinally along the central column 111 will not only cause the compression of the elastic installation element 120 to change, but will also change the position of the tensioner indicator 123 in the slot 134 of the housing 102. As such, the user is able to visually determine, via inspection of the relative position of the tension indicator 123 to the slot 134, the amount of force that will be applied to install the transcutaneous element. In this manner, the user can adjust, on the basis of this visual indication, the amount of force to be applied according to a personal preference. Furthermore, once the user knows the amount of force that satisfies their personal preference or requirements, the user can adjust different instances of the insertion device so as to apply the same amount of force. In exemplary embodiments, the slot 134 may be provided with markings (such as consecutive numbering) so as to allow for an easier visual indication of the force that will be applied by the insertion device 100 when installing the transcutaneous element of the medical device 200.

Figure 11:
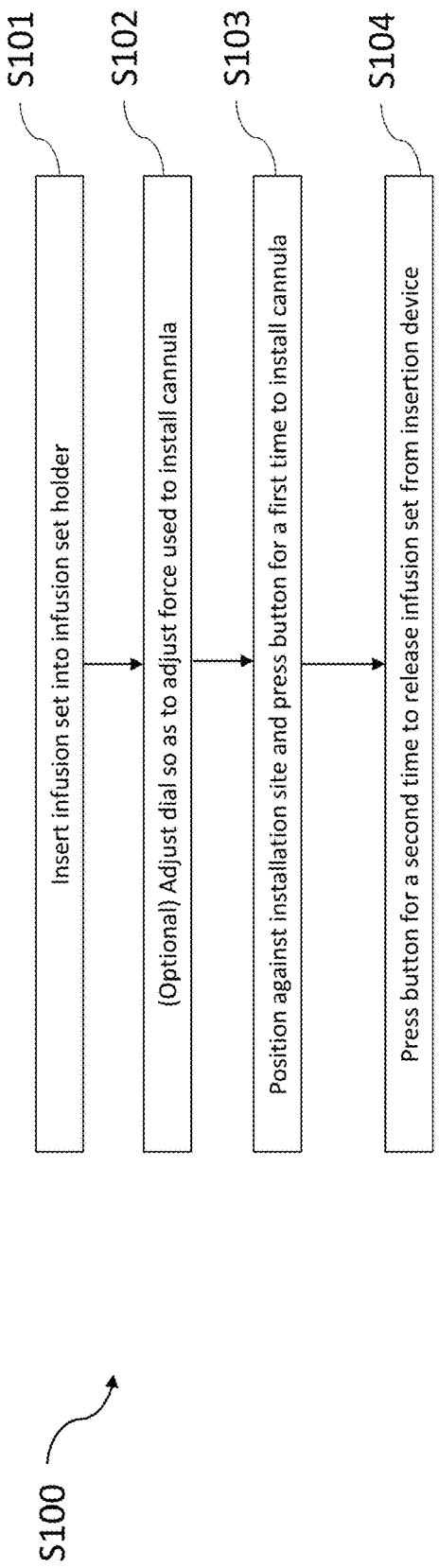
FIG. 11 shows a flowchart depicting a method in accordance with exemplary embodiments.

Use of the insertion device 100 to install a medical device 200 will now be explained with respect to the flowchart S100 shown in FIG. 11.

At step S101, a medical device, for example an infusion set, is inserted into a device holder of the insertion device. The method then proceeds to step S102.

At step S102, which is an optional step, a dial of the insertion device is adjusted so as to adjust the amount of force that will be applied by the insertion device to install a transcutaneous element of the medical device. After the user has adjusted the dial so as to satisfy personal preferences, the method progresses to step S103.

At step S103, the user positions the medical device against a desired installation site and presses a button of the insertion device for a first time to install a transcutaneous element of the medical device into the user's tissue. The method then progresses to step S104.

At step S104, the user presses the same button of the insertion device for a second time to release the medical device from the device holder to complete installation of the medical device.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, embodiments of the insertion device may include computerized or mechanized components to adjust the force used in the installation of the infusion set, which components may employ various integrated circuit components, e.g., memory elements, digital signal processing elements, logic elements, look-up tables, or the like, which may carry out a variety of functions under the control of one or more microprocessors or other control devices.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

For the sake of brevity, conventional techniques related to biosensor probe manufacturing may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

The invention claimed is:

1. An insertion device for installation of a medical device having a transcutaneous element, the insertion device comprising:
 a device holder for holding the medical device,
 an installation surface configured to contact the medical device so as to deploy the—transcutaneous element of the medical device;
 an elastic installation element configured to apply a force to the installation surface so as to bring the installation surface into contact with the medical device;
 a tensioner configured to move towards or away from the medical device to adjust the force applied by the elastic installation element to the installation surface, wherein at least a portion of the tensioner is in direct contact with the elastic installation element, and
 a button, wherein pressing the button for a first time is configured to cause ne elastic installation element to apply the force to the installation surface, and wherein pressing the button a second time is configured to cause release of the medical device from the device holder.

2. The insertion device of claim 1, wherein the installation surface is connected to one or more latches configured to be brought into mating contact with one or more corresponding recesses in a surface of an internal casing surrounding the elastic installation element, wherein, when the one or more latches are in mating contact with the one or more corresponding recesses, the elastic installation element is in a compressed state, wherein the button is connected to extension elements, and wherein pressing the button is configured to cause the extension elements to contact the one or more latches and to release the mating contact between the one or more latches and the one or more corresponding recesses.

3. The insertion device of claim 1, wherein the button is connected to a first rotation surface and wherein the installation surface is connected to a second rotation surface, and wherein the second press of the button is configured to cause the first rotation surface to move toward and to engage with the second rotation surface so as to cause rotation of the second rotation surface from an original rotation position, thereby causing rotation of the device holder so as to release the medical device from the device holder.

4. The insertion device of claim 3, wherein the device holder comprises an angled slot configured to apply a release force to the medical device held in the device holder when the device holder is rotated.

5. The insertion device of claim 3, further comprising a return element configured to return the second rotation surface to the original rotational position after the first rotation surface is brought out of contact with the second rotation surface.

6. The insertion device of claim 1, wherein the insertion device further comprises a rotating dial connected to the tensioner, the rotating dial configured to adjust a position of the tensioner, and wherein adjusting the position of the tensioner is configured to cause the adjustment of the force applied by the elastic installation element to the installation surface.

7. The insertion device of claim 1, wherein a tension indicator is connected to the tensioner, wherein the tension indicator is configured to provide a visual indication of the force applied by the elastic installation element to the installation surface.

8. The insertion device of claim 7, wherein the tension indicator is provided in a slot of an outer casing of the insertion device.

9. The insertion device of claim 1, wherein the device holder is configured to hold an infusion set comprising a cannula.

10. The insertion device of claim 1, wherein the device holder is configured to hold an analyte sensor comprising a sensor probe.

11. A method of using an insertion device to install a medical device, the method comprising:
inserting a medical device having a transcutaneous element into a device holder of the insertion device;
positioning the device holder against an installation site;
pressing a button of the insertion device for a first time to install the transcutaneous element of the medical device; and
pressing the button of the insertion device for a second time to release the medical device from the insertion device.

12. The method of claim 11, further comprising adjusting a force used to install the transcutaneous element of the medical device.

13. The method of claim 12, wherein the step of adjusting a force used to install the transcutaneous element of the medical device comprises rotating a dial of the insertion device.

14. The method of claim 13, wherein the step of rotating the dial causes movement of a tension indicator to provide a visual indication of the force used to install the transcutaneous element.

15. The method of claim 11, wherein the medical device comprises an infusion set and the transcutaneous element comprises a cannula.

16. The method of claim 11, wherein the medical device comprises an analyte sensor and the transcutaneous element comprises a sensor probe.

* * * * *